United States Patent
Allenberg et al.

[19]

[11] Patent Number: 5,913,840
[45] Date of Patent: Jun. 22, 1999

[54] SOFT ORTHOPEDIC CASTING ARTICLE WITH REINFORCEMENT SYSTEM

[75] Inventors: Kurt Allenberg, Woodbury; Joel D. Oxman, St. Louis Park; Charles C. Polta, St. Paul, all of Minn.

[73] Assignee: Minnesota Mining and Manufacturing Company, St. Paul, Minn.

[21] Appl. No.: 08/911,740

[22] Filed: Aug. 15, 1997

[51] Int. Cl.⁶ .............................. A61L 15/00; A61F 13/00
[52] U.S. Cl. .................................. 602/8; 602/8; 428/35
[58] Field of Search ................ 602/8; 525/40; 428/35

[56] References Cited

U.S. PATENT DOCUMENTS

| | | |
|---|---|---|
| 3,630,194 | 12/1971 | Boardman . |
| 3,908,644 | 9/1975 | Neinart et al. . |
| 3,954,475 | 5/1976 | Bonham et al. ............................. 96/67 |
| 3,968,791 | 7/1976 | Forsberg . |
| 4,212,970 | 7/1980 | Iwasaki .................................. 542/455 |
| 4,214,578 | 7/1980 | Gianakakos et al. . |
| 4,298,711 | 11/1981 | Moulson et al. ........................ 525/40 |
| 4,376,438 | 3/1983 | Straube et al. . |
| 4,426,504 | 1/1984 | Nandi ..................................... 526/282 |
| 4,433,680 | 2/1984 | Yoon . |
| 4,502,479 | 3/1985 | Garwood et al. . |
| 4,539,382 | 9/1985 | Omura et al. ........................... 526/276 |
| 4,609,578 | 9/1986 | Reed ........................................ 428/76 |
| 4,667,661 | 5/1987 | Scholz et al. . |
| 4,668,563 | 5/1987 | Buese et al. ............................ 428/230 |
| 4,672,956 | 6/1987 | Potter et al. . |
| 4,690,842 | 9/1987 | Kammerer et al. ....................... 428/35 |
| 4,705,840 | 11/1987 | Buckanin ................................. 528/53 |
| 4,774,937 | 10/1988 | Scholz et al. . |
| 4,899,738 | 2/1990 | Parker . |
| 4,968,542 | 11/1990 | Gasper et al. ............................ 428/76 |
| 5,014,403 | 5/1991 | Buese ........................................ 28/170 |
| 5,027,803 | 7/1991 | Scholz et al. . |
| 5,090,405 | 2/1992 | Jansen et al. .............................. 602/8 |
| 5,154,762 | 10/1992 | Mitra et al. ............................... 106/35 |
| 5,346,939 | 9/1994 | Moren et al. ............................ 524/176 |
| 5,353,486 | 10/1994 | Schmidt et al. .......................... 28/167 |
| 5,354,259 | 10/1994 | Scholz et al. ............................... 602/8 |
| 5,364,693 | 11/1994 | Moren et al. ............................ 428/263 |
| 5,405,643 | 4/1995 | Scholz .................................... 427/2.31 |
| 5,423,735 | 6/1995 | Callinan et al. ............................ 602/8 |
| 5,474,522 | 12/1995 | Scholz et al. ............................... 602/8 |
| 5,545,676 | 8/1996 | Palazzotto et al. ...................... 522/15 |

FOREIGN PATENT DOCUMENTS

| | | |
|---|---|---|
| 0 086 621 | 8/1983 | European Pat. Off. . |
| 0 407 056 A2 | 1/1991 | European Pat. Off. . |
| WO 88/05652 | 8/1988 | WIPO . |
| WO 94/25076 | 11/1994 | WIPO . |

OTHER PUBLICATIONS

Noller, Carl R. ,*Chemistry of Organic Compounds*, Second Edition, 1957, pp. 121–122.

*Primary Examiner*—Jerome W. Donnelly
*Assistant Examiner*—Kelvin Hunt
*Attorney, Agent, or Firm*—F. Andrew Ubel

[57] ABSTRACT

The present invention provides a reinforceable orthopedic casting article comprising a backing and a curable resin having an activator capable of assisting in the initiation of the cure of an addition polymerizable reinforcement compound. Reinforced casts are made by providing a curable casting tape comprising a backing and a curable resin containing an activator capable of assisting in the initiation of the cure of an addition polymerizable reinforcement compound; initiating the cure of the casting tape; wrapping the casting tape into the form of a cast; applying a hardenable reinforcement compound to at least a portion of the casting tape; and allowing the casting tape to cure and the reinforcement compound to harden to form a reinforced orthopedic cast. In another method a reinforced soft cast is made by wrapping a soft casting tape into the form of a cast, wherein the casting tape comprises a backing and a curable resin; initiating the cure of the casting tape; applying an activated addition polymerizable reinforcement compound to at least a portion of the casting tape; and allowing the casting tape to cure and the reinforcement compound to harden to form a reinforced orthopedic cast.

19 Claims, 3 Drawing Sheets

SOFT ORTHOPEDIC CASTING ARTICLE WITH REINFORCEMENT SYSTEM

FIELD OF THE INVENTION

This invention relates to orthopedic casting materials.

BACKGROUND OF THE INVENTION

Many different orthopedic casting materials have been developed for use in the immobilization of broken or otherwise injured body limbs. Some of the first casting materials developed for this purpose involved the use of plaster of Paris bandages consisting of a cotton gauze mesh fabric with plaster incorporated into the openings and onto the surface of the mesh fabric. Plaster of Paris casts, however, have a number of attendant disadvantages, including a low strength-to-weight ratio, resulting in a finished cast which is very heavy and bulky. In addition, plaster of Paris casts develop their strength over a relatively long period of time, thus making it necessary to avoid weight bearing situations for up to 24 to 48 hours. Furthermore, plaster of Paris casts typically disintegrate in water, thus making it necessary to avoid bathing, showering, or other activities involving contact with water.

A significant advancement in the art was achieved when synthetic polyisocyanate prepolymers were found to be useful in orthopedic casting materials. Typical commercially available synthetic casting materials comprise a knit fiberglass fabric backing impregnated with a polyisocyanate prepolymer resin. These casting materials can provide significant advancement over the plaster of Paris casts, including a higher strength-to-weight ratio. Unfortunately, however, knitted fiberglass backings of conventional casting articles may become quite rough when cured and often produce casts with sharp edges. The sharp edges can cause skin abrasions and/or snag clothing. As a result, the health care worker has had to employ padding materials at the edges to attempt to avoid contact of the casting article with the skin.

A modified synthetic casting material was developed for use in non-weight bearing applications. These softer, more flexible casting materials (e.g., "SOFTCAST" from 3M) are typically used for functional immobilizations that can tolerate some movement (e.g., non-serious, minor broken bones; or more typically strains, sprains, and ligament damage). Recently, these softer materials have been used together with the conventional harder, stiffer casting tapes for functional immobilization. In a typical use, one or more strips of the harder, stiffer casting tape are laid down on the surface of the cast and covered with additional layers of the softer more flexible material. This application technique is somewhat cumbersome, and requires the health care worker to handle two different casting tapes. Furthermore, generally only a portion of a roll of the harder, stiffer material is needed for the reinforcement. The remainder is generally wasted as it will cure within a short time after having been taken from its pouch.

SUMMARY OF THE INVENTION

From the foregoing, it will be appreciated that what is needed in the art is a soft, comfortable casting material that can be selectively reinforced to provide sufficient support to the injured limb. Also needed is an easy method of selectively reinforcing a soft casting material. Such orthopedic casting materials and methods for preparing and using the same are disclosed and claimed herein.

In one embodiment the present invention provides a reinforceable orthopedic casting article (e.g., a casting tape or splint) that comprises a backing (e.g., a knit fiberglass) and a curable resin (e.g., a water-curable resin) having an activator. The activator is capable of assisting in the initiation of the cure of an addition polymerizable reinforcement compound.

Methods of making reinforced orthopedic casts are also provided. In one method the reinforced cast is made by providing a curable casting tape comprising a backing and a curable resin containing an activator capable of assisting in the initiation of the cure of an addition polymerizable reinforcement compound; initiating the cure of the casting tape; wrapping the casting tape into the form of a cast; applying a hardenable reinforcement compound to at least a portion of the casting article; and allowing the casting tape to cure and the reinforcement compound to harden to form a reinforced orthopedic cast. In another method a reinforced soft cast is made by wrapping a soft casting material into the form of a cast, wherein the casting tape comprises a backing and a curable resin; initiating the cure of the casting tape; applying an activated addition polymerizable reinforcement compound to at least a portion of the casting article; and allowing the casting tape to cure and the reinforcement compound to harden to form a reinforced orthopedic cast.

The present invention also provides kits for making reinforced orthopedic casts. The kit contains a casting tape comprising an activator; and a reinforcement compound. The activator provided with the casting tape is present in a sufficient quantity to cause hardening of the reinforcement compound when the reinforcement compound is applied to the casting tape.

DEFINITIONS

A "casting material" refers to a material (e.g., a composite material, a resin coated sheet, etc.) that undergoes a change of state from a generally moldable first state to a generally nonmoldable second state, thereby allowing the formation of a customizable support device.

A "reinforcement compound" or "reinforcement composition" refers to a compound or composition (e.g., a liquid or paste compound, etc.) that undergoes a change of state from a generally flowable first state to a generally nonflowable second state, thereby allowing the reinforcement of a region of a support device. Unless otherwise indicated, the terms "compound" and "composition" are used interchangeably.

The "support devices" of the present invention (e.g., casting tapes or splints) are characterized as having at least one "soft region" and at least one "reinforced region." The second states of the soft region and the reinforced region differ in at least one physical property, with the reinforced region being at least discernibly more rigid, less resilient or harder than the soft region.

The term "differential hardness" refers to the relative difference in rigidity, resilience, or hardness between the unreinforced soft region and the reinforced region of a casting tape or splint (i.e., the relative difference between the second states of the two regions).

The "soft region" of a support device is the unreinforced region of the support device that comprises a soft casting material. A "soft casting material" refers to a casting material that undergoes a change of state from a generally moldable first state to a second state comprising a generally semi-rigid, resilient, or soft support device. A soft casting material includes, for example, a soft resin coated on a backing. A "soft resin" refers to a curable resin system that, when coated or otherwise applied onto a backing and cured, forms a generally semi-rigid, resilient, or soft support device.

The "reinforced region" of a support device is the region of the support device that has been reinforced with a reinforcement compound.

A "hard casting material" refers to a casting material that undergoes a change of slate from a generally moldable first state to a second state comprising a generally rigid, non-resilient, or hard support device. A hard casting material generally includes a hard resin coated on a backing. A "hard resin" refers to a curable resin system that, when coated or otherwise applied onto a backing and cured, forms a generally rigid, non-resilient, or hard support device. More preferably, the hard resin, when coated and cured onto a traditional fiberglass backing, provides a rigid support device that can support without further reinforcement the weight normally carried by the limb around which the support device is wrapped.

A "curable resin system" refers to any type of resin system that undergoes a change of state from a generally flowable or moldable uncured first state to a generally nonflowable or nonmoldable cured second state.

The terms "backing", "carrier", and "scrim" refer to the structure upon which one or more curable resins may be coated or otherwise applied. A "fabric backing" is a backing that comprises a knit, woven or nonwoven fabric material.

The term "associated with" refers to the intimate relationship between the resin system and the backing, such as may be accomplished, for example, by coating a backing with a resin and/or impregnating a backing with a resin.

BRIEF DESCRIPTION OF THE DRAWINGS

The invention may be more clearly understood by reference to the drawings, wherein:

FIG. 1 shows a partially unwound roll 10 of casting tape 20 in perspective view. The partially unwound sheet is shown with a first edge 15, a second edge 17, and a first end 13. A second end 19 is wound around the core of the roll and is not in view.

FIG. 2 illustrates a human arm wrapped with the casting tape of FIG. 1. Often, the casting tape 20 comprises a backing and a curable resin coated on the backing.

FIG. 3 illustrates a human arm wrapped with the casting tape of FIG. 1 and having a portion 40 of the cast reinforced with a reinforcement compound 41.

FIG. 4a shows a splint article 310 having a thumb hole 311. FIG. 4b shows the splint article 310 of FIG. 4a adapted to a human arm. An optional padding material 330 is wrapped or placed on the arm prior to placement of the splint article 310. FIG. 4c shows the adapted splint article 310 adapted to a human arm and having a portion 320 of the splint reinforced with a reinforcement compound 321. FIG. 4d shows an overlay bandage 340 wrapped around the human arm and over the splint article 310 of FIG. 4c, thereby securing the splint article 310 to the arm.

Figure 1:
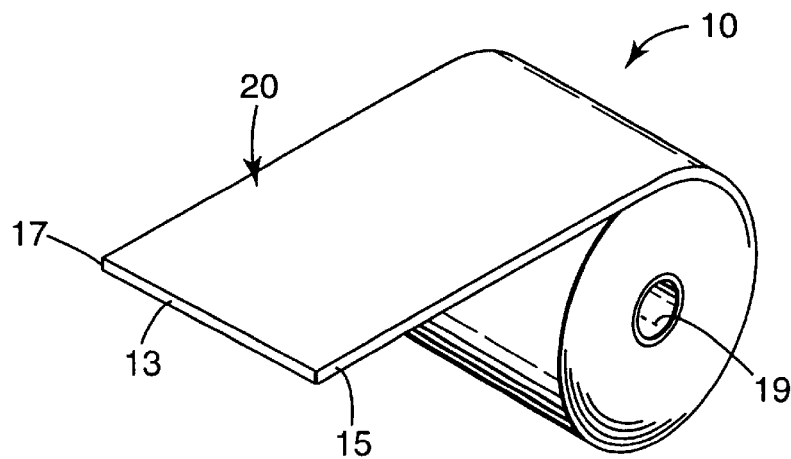
FIG. 1 shows a partially unwound roll of casting tape.
Figure 2:
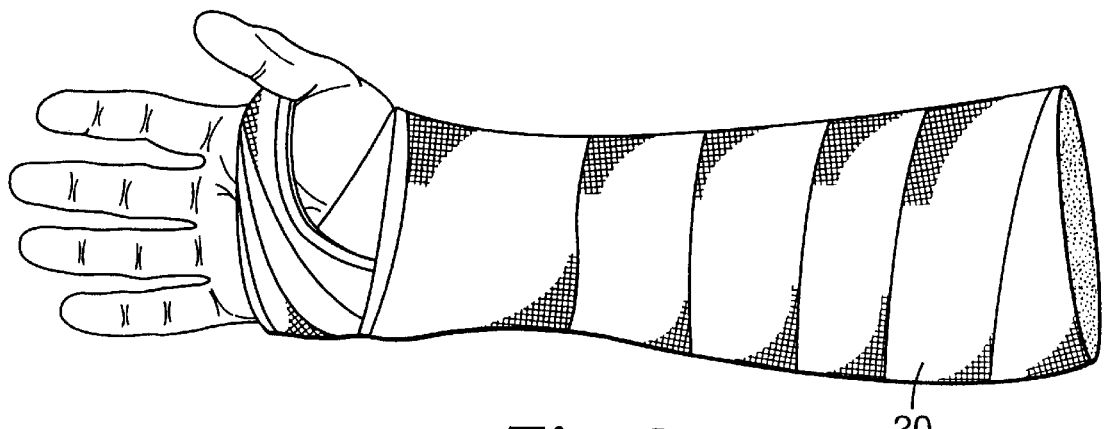
FIG. 2 shows a human arm wrapped with the casting tape of FIG. 1.
Figure 3:
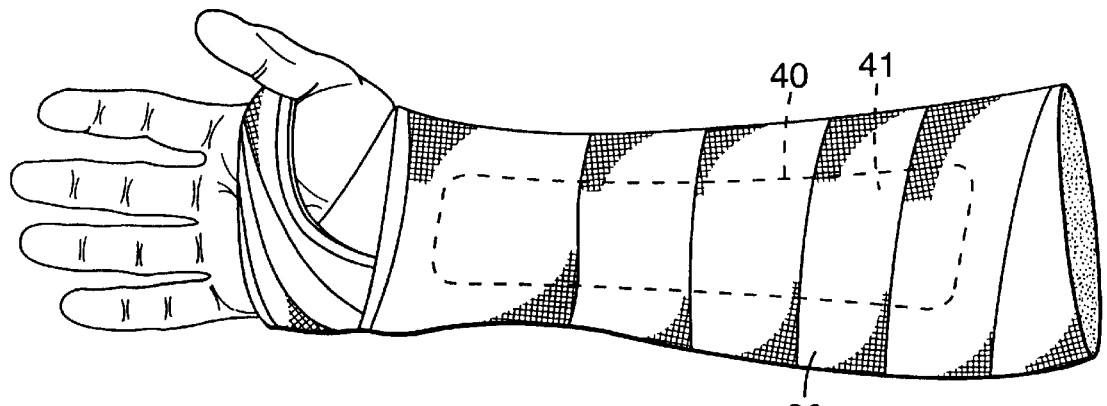
FIG. 3 shows a human arm wrapped with the casting tape of FIG. 1 and having a portion of the cast reinforced with a reinforcement compound.

This invention utilizes certain principles and/or concepts as are set forth in the claims appended to this specification. Those skilled in the casting arts to which this invention pertains will realize that these principles and/or concepts are capable of being illustrated in a variety of embodiments which may differ from the exact embodiments utilized for illustrative purposes in this specification. For these reasons, the invention described in this specification is not to be construed as being limited to only the illustrative embodiments but is only to be construed in view of the appended claims.

DETAILED DESCRIPTION OF THE INVENTION

The present invention provides a curable orthopedic support device comprising a casting material, preferably a soft casting material, and a reinforcement compound applied to the casting material. When cured, the reinforcement compound reinforces the support device in those areas where it is applied. In one presently preferred embodiment, the casting material comprises a flexible backing associated with a curable resin system which cures upon exposure to a curing agent. A reinforcement compound comprising, for example, a redox activated resin system, is applied to the casting material (e.g., after the casting material is applied to a patient's limb) and allowed to harden, thereby forming a reinforced region of the support device. The casting material is preferably stored prior to use in a package that prevents contact of the resin with the curing agent and the reinforcement compound is preferably packaged in a container that facilitates easy application to the casting material. The invention also relates to the method of applying the support device, and to the cured device so formed.

Preferably, the orthopedic support device is in the form of an orthopedic casting tape comprising a fabric backing that is associated with a curable resin. In one embodiment, the curable resin comprises an activator that facilitates or causes the curing of the reinforcement compound upon application of the compound to the casting material. The reinforcement compound may alternatively or additionally be self activated. For example, the reinforcement compound may comprise a two-part composition that is activated upon being mixed together.

Suitable curable resins for use in the casting materials of the present invention include any curable resins which will satisfy the functional requirements of an orthopedic cast. Obviously, the resin preferably is nontoxic (e.g., not give off significant amounts of toxic vapors during curing which may be harmful to either the patient or the person applying the cast); and not cause skin irritation (e.g., either by chemical irritation or the generation of excessive heat during cure). Furthermore, the resin must be sufficiently reactive with the curing agent to insure rapid curing of the cast once it is applied but not so reactive that it does not allow sufficient working time to apply and shape the cast. Initially, the casting material must be pliable and formable and should adhere to itself. Then in a short time following completion of cast application, it should become rigid enough and strong enough, when reinforced as described herein, to support loads and stresses to which the cast is subjected by the activities of the wearer.

The following disclosure relates primarily to the presently preferred embodiments of the invention wherein water-curable isocyanate-functional prepolymers are employed as the curable resin. Other suitable curable resins may be used and are discussed later.

The casting tape is preferably a backing that is coated with a "soft resin." Some presently more preferred soft resins are the water-curable, isocyanate-functional prepolymers disclosed, for example, in U.S. Pat. No. 4,968,542, the disclosure of which is herein incorporated by reference.

A "water-curable isocyanate-functional prepolymer" means a prepolymer derived from a polyisocyanate compound and a reactive hydrogen compound or oligomer (e.g., a "polyol"). A reactive hydrogen compound is a compound having active hydrogen in accordance with the well known Zerevitinov test as described, for example, in Chemistry of Organic Compounds by Carl R. Noller, Chapter 6, pp. 121–122 (1957). The prepolymer has sufficient isocyanate-functionality to cure upon exposure to water, e.g., moisture vapor, or preferably liquid water. It is presently preferred to employ a polyisocyanate prepolymer formed by the reaction of an isocyanate and a polyol.

The presently most preferred soft resins include moisture-curing polyurethane prepolymers prepared by the reaction of a polyol with an excess of polyisocyanate. The starting materials are from the same chemical classes as those used to form the typical rigid (or "hard") polyurethane casting materials well known in the art as described in U.S. Pat. Nos. 4,376,438, 4,433,680, 4,502,479, and 4,667,661, which are herein incorporated by reference. However, the isocyanate equivalent weights of the prepolymers and/or the average hydroxy equivalent weight of the polyol are preferably modified to obtain the desired semi-rigid properties. Additionally, other active hydrogen materials may be used alone or in conjunction with polyols to produce soft resins which will be useful in this invention. Examples are primary and secondary amines, carboxylic acid and thiols.

Suitable isocyanates include those disclosed, for example, in U.S. Pat. Nos. 4,376,438, 4,433,680, and 4,502,479, and include: 2,4-toluene diisocyanate, 2,6-toluene diisocyanate, and mixtures of these isomers; 4,4'-diphenylmethane diisocyanate, 2,4'-diphenylmethane diisocyanate, and mixtures of these isomers together with possible small quantities of 2,2'-diphenylmethane diisocyanate (typical of commercially available diphenylmethane diisocyanate); and aromatic polyisocyanates and mixtures such as are derived from phosgenation of the condensation product of aniline and formaldehyde. It is preferred to use an isocyanate which has low volatility such as diphenylmethane diisocyanate (MDI) rather than a more volatile material such as toluene diisocyanate (TDI). Suitable commercially available isocyanate starting materials include "ISONATE" 2143L (available from Dow Chemical Co.), "MONDUR" MRS (Mobay Chem. Co., Pittsburgh, Pa.), and "PAPI" (Dow Chemical Co.).

The degree of rigidity and resiliency in the cured support device is generally determined by the average hydroxy equivalent weight of the polyol or polyol blend. The choice of hydroxy equivalent weight is also dependent upon the molecular structure and type of the isocyanate.

Suitable polyols for use in the prepolymer resin system include polyalkylene oxides (e.g., polyethylene oxide and polypropylene oxide), polyalkylene ethers derived from the condensation of alkylene oxides (such as those available from Arco Chemical under the tradename "ARCOL PPG," and from BASF Wyandotte under the tradename "PLURACOL"), polytetramethylene ether glycols (such as "POLYMEG" from the Quaker Oats Co. or "TERATHANE" from the Du Pont de Nemours, E.I., Co., Wilmington Del.), polycaprolactone polyols (e.g., "TONE" series of polyols from Union Carbide), and polyester polyols (e.g., hydroxyl-terminated polyesters obtained from esterification of dicarboxylic acids and diols such as the "RUCOFLEX" polyols available from Ruco division, Hooker Chemicals Co.). In general, by using higher molecular weight polyols, the rigidity of the cured resin can be decreased.

An especially preferred resin for use in the support materials of the invention uses an isocyanate known as "ISONATE" 2143L available from Dow Chemical (a mixture of isocyanate compounds containing about 73% by weight of diphenylmethane diisocyanate) and a mixture of polypropylene oxide polyols available from Arco Chemical as ARCOL LHT-28, LHT-42 and PPG 425. To prolong the shelf-life of the materials, it is preferred to include about 0.02–0.1 percent by weight of benzoyl chloride and/or other suitable stabilizer (e.g., an antioxidant such as butylated hydroxy toluene at a level of about 0.05 to 0.25 weight percent).

The isocyanates and the polyols are reacted with one another under conventional polyurethane reaction conditions known to those skilled in the art. The NCO:OH ratio of the reactants is in the range of about 1.5:1 to 7.0:1 and preferably between 2.5 and 4.5:1.

In general, the softness of a resin may be affected by adjusting the "functionality" of the reactants. As the functionality increases, e.g., as the relative amount of tri-functional material compared to di-functional material is increased, the softness will decrease. However, the elasticity or resilience of the material may increase somewhat. Also, in general, the softness of a resin may be affected by adjusting the "equivalent weight" of the reactants. As the equivalent weight increases, e.g., as the equivalent weight of polyol is increased, the softness will increase.

To form a presently preferred soft resin, the theoretical isocyanate equivalent weight of the prepolymer preferably is greater than about 400 grams, more preferably greater than about 500 grams, and most preferably greater than about 1000 grams. Preferably the theoretical polyol equivalent weight of the prepolymer is greater than about 400 grams, more preferably greater than about 500 grams, and most preferably greater than about 1000 grams. Of course these weights might be different were the resin to contain an adjuvent such as a plasticizer or utilize a different NCO:OH ratio or average functionality of reactants.

The reactivity of the resin once it is exposed to the water curing agent can be controlled by the use of a suitable amount of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]-morpholine ("MEMPE") prepared as described in U.S. Pat. No. 4,705,840 and 2,2'dimorpholinodiethyl ether ("DMDEE") prepared as described in U.S. Pat. No. 4,433, 680, the disclosures of which are incorporated by reference, at a concentration of about 0.05 to about 5 percent by weight (based on total resin weight). To produce the cured support devices of the present invention, a cure time of about 2.5 to 18 minutes following exposure to the curing agent, e.g., dipping in water, is preferred. More preferably, the cure time is between about 3 and 10 minutes, and most preferably between about 3 and 5 minutes.

In general, foaming of the resin preferably should be minimized since it may adversely impact the surface smoothness of the cast and may decrease the cast's overall strength. Foaming may occur, for example, when carbon dioxide is released as a result of water reacting with an isocyanate group. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. A satisfactory method of minimizing foaming is to add a foam suppresser such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polymeric particles, such as disclosed in European Published Patent Application EPO 0 407 056, may also be used to reduce foaming.

If desired, however, foaming of the resin may be used to advantage. For example, foaming may have a desired effect of lowering the rigidity of the casting tape. The foaming may be adjusted by coating the tape with a resin that does not have an anti-foam agent (thereby allowing foaming to occur naturally during cure of the resin) or by coating the region with a resin that contains a foaming agent such as GR-5M triton surfactant from Union Carbide.

Lubricants are preferably added to the resin or resins, e.g., as described in U.S. Pat. Nos. 4,667,661 and 4,774,937, which are herein incorporated by reference, such that the casting materials exhibit reduced tack prior to and during cure and yet form a cast with acceptable strength. This is especially true for the soft resins used in the present invention. These resins tend to be even more sticky than those used to form rigid casts. Suitable lubricants include: hydrophilic groups which are covalently bond to the resin system; additives which are nonreactive with the curable resin including surfactants, polymers comprised of a plurality of hydrophilic groups, and polysiloxanes; and combinations of the above. If desired, the lubricant may be used in conjunction with a separate fugitive liner such as are disclosed in U.S. patent application Ser. No. 08/404,242, which is herein incorporated by reference.

The preferred method of detackifying the polyurethane prepolymer resin systems involves the addition of a lubricant, especially a surfactant, to the system. The preferred surfactants are block copolymers of propylene oxide and ethylene oxide or polyethylene oxides which are solids at 23° C. in an amount ranging from 3 to 6 percent by weight of the prepolymer system. Especially preferred are hydroxy functional polyethylene oxide terminated polypropylene oxides (sold under the tradename "Pluronic" by BASF Wyandotte).

Plasticizers may be added to the resin to adjust the cured resin's hardness. Suitable plasticizers are well known in the art and are preferably added to the soft resin in amounts that provide the desired level of softness to the cured article. Preferably, the plasticizer does not adversely affect the shelf stability of the uncured casting tape or otherwise negatively impact the physical or toxicological properties of the material. Suitable plasticizers include materials such as Butyl Benzolphalate, Santicizer 160, from Monsanto Chemical Co.

Presently preferred resins are the aforementioned urethane resins formed by the reaction of a polyisocyanate and a polyol. Other water-curable resins known in the art (optionally combined with moisture sensitive catalysts) may be suitable, including polyurethanes, cyanoacrylate esters, epoxy resins and prepolymers terminated at their ends with trialkoxy- or trihalo-silane groups. Resin systems other that those which are water-curable may be used, although the use of water to activate the hardening of an orthopedic casting tape is most convenient, safe and familiar to orthopedic surgeons and medical casting personnel. Preferred resins are not appreciably dispersible in water. Suitable water-activated and alternative curing resins include moisture-curing polyurea prepolymers, silane, siloxane, epoxy, acrylate, polysulfide and polyester functional materials. Light-curing materials such as certain active olefins, e.g., acrylates and pendant vinyls, are also candidates.

Suitable resins include those disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol). The resin may be hardened upon wetting with solutions of a tertiary amine and an organic peroxide. Alternatively, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system).

Also included as resins in this invention are water curable alkoxy silane terminated oligomers such as are disclosed in U.S. Pat. No. 5,423,735 which is herein incorporated by reference.

Also included as resins in this invention are water reactive liquid organometallic compounds such as are disclosed in pending U.S. Pat. Nos. 5,364,693 and 5,346,939, which are herein incorporated by reference. These resins generally consist of a water-reactive liquid organometallic compound and an organic polymer.

The backing used in the support material of the present invention is preferably porous such that the sheet is at least partially impregnated with the resin. A porous sheet material also facilitates circulation of air through the cured device and evaporation of moisture from beneath the device. This contributes to the patient's comfort and to the maintenance of healthy skin under the device.

Examples of suitable flexible sheet materials include woven or knit fabrics comprised of natural or synthetic fibers such as polyamide, polyester, polyolefin, polyacrylamide, etc. Preferred sheet materials are extensible knit fabrics of fiberglass or polyester. Suitable fiberglass fabrics are disclosed in U.S. Pat. Nos. 4,502,479, 4,609,578, 4,668,563, 5,014,403, 5,353,486 and 5,405,643, which are herein incorporated by reference. Particularly preferred sheets of this type are extensible, heat-set fabrics as disclosed in U.S. Pat. No. 4,609,578.

Preferred sheet materials used in the casting tapes of the present invention are generally long, narrow fabric strips (tapes) wound in rolls of various widths, e.g., from about 5 cm to about 15 cm wide. The fabric is impregnated with the curable resin material in an amount of about 30 to 80 percent by weight of the support material, and in the preferred embodiment, employing a fiberglass fabric, of from 40 to 60 percent by weight of the impregnated support material. The term "impregnate" is used to describe the condition in which the resin is thoroughly intermingled with and in surrounding relation to the threads or fibers of the fabric and does not necessarily indicate that the resin is to any extent absorbed by the fibers themselves. Generally, the resin solution will flow into the capillary spaces between contiguous filaments of the fabric and will become bonded to the fabric upon curing.

The amount of resinous component applied to the fabric must be sufficient for the formation of an interlayer laminate bond, but preferably not so much as to occlude the porosity. Excessive resinous component may also cause the support material to be messy to handle due to stickiness or dripping of the resin.

The resin coated fabric strips in roll form are preferably wound on a plastic core and sealed within a moisture and oxygen impermeable package. In the case of moisture-curing resins, the package is opened immediately before use and the roll is fully immersed in tap water for about 5 to 30 seconds. This is sufficient time for water to seep into the porous material and displace air. As long as the resin content is not so high as to cause the openings in the fabric to be filled with resin, more than enough water is absorbed by the roll in this manner. The roll may be squeezed underwater to replace entrapped air with water. When the roll is unwound during wrapping of the material, the excess moisture coats freshly exposed resin surfaces insuring thorough wetting and rapid curing of the material. An alternate method comprises wrapping the material without dipping and then allowing atmospheric moisture or water provided by spraying or by application of a wet towel to cure the prepolymer.

Prior to applying the support material, protective padding is optionally positioned about the limb of the patient. The padding may take the form of a tubular stockinet or some other convenient form, such as for example, an elongated strip or bandage which may be wrapped about the body member.

With the padding in proper position, the moistened support material is wrapped about the limb and over the protective padding in a manner similar to the application of a standard casting material. The material is also shaped in a manner similar to the shaping of a rigid synthetic or plaster cast. However, unlike a standard casting procedure the support material is reinforced at various regions using the reinforcement compounds described herein.

Eight or fewer layers of the support material should generally be sufficient, when augmented by the reinforcement compound, to form a cured device providing adequate support and/or immobilization for most applications.

The materials and compositions of the present invention may be fabricated into a variety of configurations including splints, tapes, and preformed shapes.

As previously mentioned, preferred casting tapes are generally long, narrow fabric strips formed in rolls of various widths, e.g., from about 5 cm to about 15 cm wide.

The present invention also is suitable for forming a reinforced orthopedic splint around a portion of an animal body part. When fabricated as a splint, the material may be provided as a precut slab (e.g., as illustrated in FIGS. 4a–d) or a continuous length form. Furthermore, the splint may be provided with or without a covering and/or padding. Suitable coverings and paddings for use in this invention are discussed in U.S. Pat. Nos. 5,027,803 and 4,899,738 which are herein incorporated by reference. The splint may have a padding material on one or both sides.

According to a present preferred embodiment of the invention, a splint is provided which comprises a pliant, preferably extensible, and highly conformable substrate. The splint is dimensioned in a first direction sufficient to extend the length of the body part and is dimensioned in a second direction sufficient to extend partially, but preferably not completely, around the circumference of the body part. In this regard, the splint is dimensioned in the second direction so as to envelop the body part to the extent that is needed to support and immobilize the body part, while still accommodating for the swelling which generally occurs as a result of a fresh fracture or soft tissue injury.

The splint preferably comprises a backing and a soft resin impregnated into the backing.

Figure 4A:
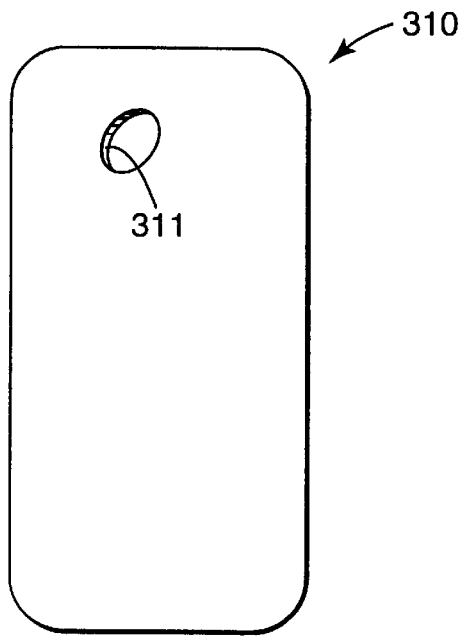
FIG. 4a shows a splint article.
Figure 4B:
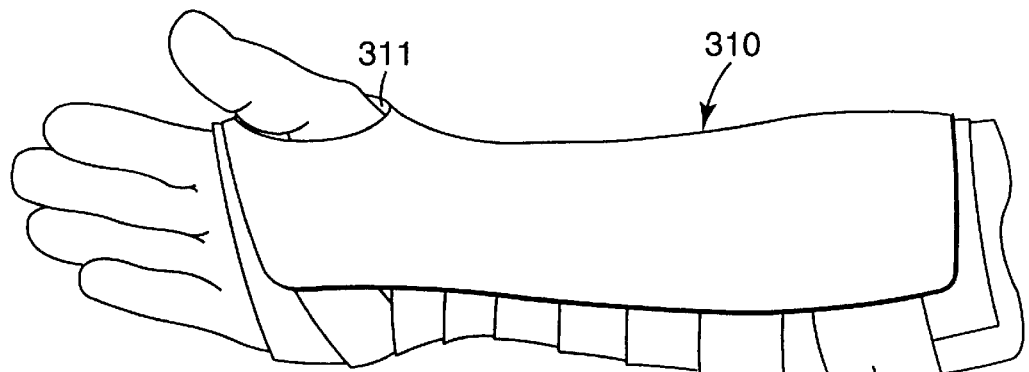
FIG. 4b shows the splint article of FIG. 4a adapted to a human arm.
Figure 4C:
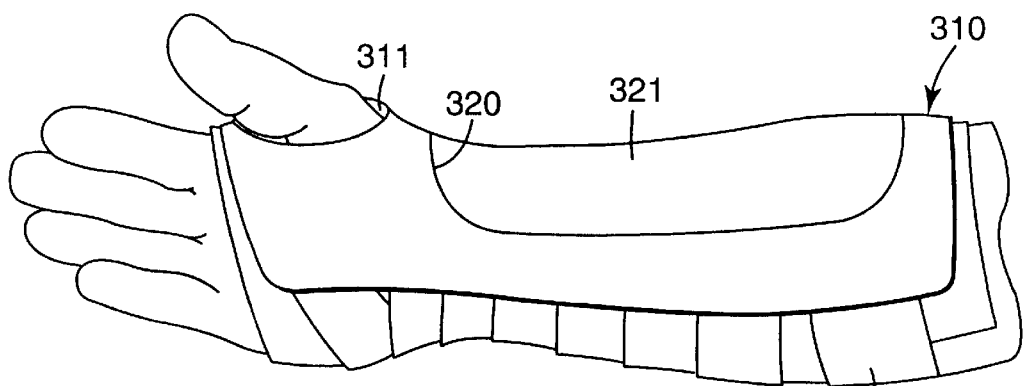
FIG. 4c shows the adapted splint article of FIG. 4a adapted to a human arm and having a portion of the splint reinforced.
Figure 4D:
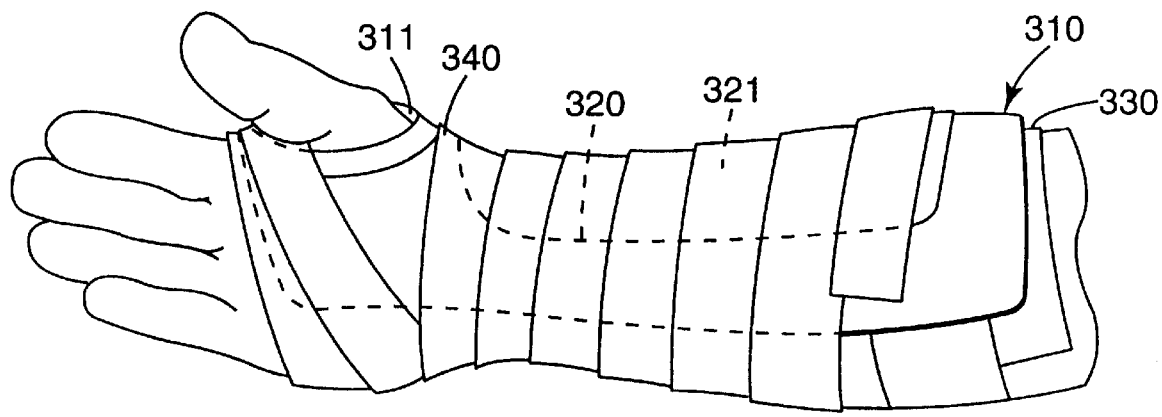
FIG. 4d shows an overlay bandage wrapped around a human arm and over the splint article of FIG. 4c.

FIG. 4a is a plan view of a preferred forearm embodiment of the orthopedic splinting article of the present invention prior to application to a limb; FIG. 4b is a plan view of a preferred forearm embodiment of the orthopedic splinting article of the present invention after application to a limb but prior to application of a reinforcement compound; FIG. 4c is a plan view of a preferred forearm embodiment of the orthopedic splinting article of the present invention after application of a reinforcement compound; and FIG. 4d is a perspective view of the embodiment of FIG. 4c additionally showing a bandage which may be optionally wrapped around the splinting article in order to provide better conformability and attachment of the splinting article to the forearm.

Referring now to FIG. 4a, there is shown in plan view a preferred forearm orthopedic splinting article 310 of the present invention. The splinting article 310 is generally comprised of a pliant sheet and preferably has a thumbhole 311 formed therein to facilitate application of the article 310 around a wearer's forearm. Article 310 may be initially configured as a rectangle, and then be trimmed to custom fit the patient. In this regard, the physical characteristics of the sheet material preferably allow for easy trimming.

The sheet of article 310 preferably includes a suitable backing and a curable soft resin associated with the backing. Suitable backings include knit, woven or nonwoven fabric materials, open-celled foam sheets, and the like.

For the forearm splint embodiment of FIGS. 4a–d, a sheet approximately 18 cm wide, and 30 cm long is presently preferred. For the lower leg embodiment, a foam sheet approximately 25 cm wide and 100 cm long is presently preferred. However, it will be appreciated that the exact dimensions employed may vary according to the respective limb sizes of the individual to be treated.

The orthopedic splinting article 310 is sized according to the forearm of the patient, and may be trimmed prior to application in order to provide a more exact fit. The thumbhole 311 may be formed by either punching or cutting out a corresponding portion of article 310.

Before actually applying article 310 to the forearm, a flexible stockinet and optionally cast padding 330 is preferably placed around the patient's forearm so as to prevent undesirable adhesion or contact between the splint and forearm of the patient. For example, a tubular padding material, such as one side lofted tubular fabric made on an athletic sock machine available from Broadway Knitting Mills, 2152 Sacramento Street, Los Angeles, Calif. 90021, may be used for this purpose.

The splint of FIGS. 4a–d is formed by first activating the resin of article 310 of FIG. 4a with water. Next, the left or right hand thumb of the patient is passed through aperture 311, and the long edge of the rectangular article is longitudinally aligned with the patient's forearm. The article is then circumferentially molded or positioned around the forearm to the position shown in FIG. 4b. In this regard, the resin impregnated sheet has excellent compression moldability or conformability to provide a good fit around the patient's forearm. Then a reinforcement compound is applied to the splint to form a reinforced region 320.

The article 310 is sufficiently dimensioned in its longest direction to extend the length of the forearm to be immobilized by the splint. The article 310 is dimensioned in the other direction so as to accommodate swelling of the forearm. This is preferably done by configuring article 310 so that it extends partially, but not completely, around the circumference of the forearm. In this regard, in order to accommodate the swelling of the forearm, the orthopedic splint 310 preferably extends around about 40% to about 90% of the circumference of the forearm, and most preferably around about 60% to about 75% of the circumference of the forearm. Such partial enclosure allows for swelling of the injured forearm, yet provides adequate immobilization thereof to promote healing.

However, it will be appreciated that the splinting article could also be configured in the circumferential direction so as to completely surround the forearm if desired. In order to accommodate swelling in such an instance, it is important that there remain a longitudinal break in the splinting article. Thus, although not the presently preferred embodiments, the splinting article could be merely wrapped around the forearm until the longest edges come into close proximity or even meet (without sealing the edges), or alternatively, so that the longest edges actually overlap slightly, but again without sealing the edges together so that the splint could still expand to accommodate swelling. Means to prevent sealing of the edges include the use of a nonadhering layer inserted between overlapping edges.

The reinforced region should be sized and positioned to provide the necessary degree of support for the limb. The exact size and position will vary depending on the particular application. In one embodiment, the reinforced region extends nearly the full length of the splint and covers approximately 50% of the circumference of the splint.

The orthopedic splinting article 310 is preferably held in place while the resin is curing by the aid of securing means. For example, wrapping means such as a stretch bandage 340 shown in FIG. 4d may be used to secure article 310 around the forearm during curing so that the resultant orthopedic splint will conform well to the forearm.

After the splint has served its intended purpose, the splint can be removed from the patient's forearm by unwrapping the stretch bandage and then prying open the splint. The general U-shape of forearm splint 310 has been found to exhibit excellent strength and resistance to breakage.

In summary, the orthopedic splinting article 310 of the present invention can be applied to a forearm by: (1) exposing the article to water to initiate hardening of the curable soft resin, (2) manually squeezing out excess water, (3) properly positioning the orthopedic splinting article over a stockinet and an optional cast pad applied to the forearm, (4) applying a reinforcement compound to the splinting article; (5) trimming the orthopedic splint to the desired shape, and (6) holding the splint in place as the splint cures, e.g., by wrapping a stretch bandage or other securing means around the splint article and forearm to secure the splint in place.

If desired the casting articles of the present invention may comprise fillers or other additives. Suitable fillers for use in the present invention include inorganic or organic, particulate or fibrous materials such as are described in U.S. patent application Ser. No. 08/463,993, the disclosure of which is herein incorporated by reference. Colored pigment fillers and blends of fillers may also be suitable.

Preferred particulate fillers have an average particle diameter less than 500 $\mu$m, more preferably less than 200 $\mu$m, and most preferably less than 120 $\mu$m. As used herein, "average particle diameter" is defined as the diameter of a sphere of the same volume as the particle.

Microfibers (such as are described in U.S. Pat. Nos. 5,474,522 and 5,354,259, the disclosure of which are herein incorporated by reference) may be added to the resin to enhance web integrity or composite strength. Preferred fibers have an average length between 25 and 5,000 $\mu$m, more preferably between 30 and 1,000 $\mu$m, and most preferably between 30 and 500 $\mu$m.

Preferred fillers and microfibers for use with water curable resins also have very low moisture content to avoid premature curing of the article. Preferably the filler or microfiber contains less than 4% by weight absorbed water, more preferably less than 1% by weight absorbed water, and most preferably less than 0.5% by weight absorbed water. The amount of absorbed water in a filler or microfiber sample may be determined by heating the sample in an oven and measuring the sample's weight loss. For fillers or microfibers that have a high amount of moisture one may preferably dry the material prior to incorporation into the resin.

If desired, the fillers or microfibers may be surface treated using silanes, titanates, zirconates and the like to enhance resin bonding, ease of mixing, and compatibility. The surface treatment may be performed prior to incorporation of the filler or microfiber into the resin or in-situ, i.e., the surface treatment agent may be incorporated into the resin for later reaction with the filler or microfiber.

The shelf stability of the uncured casting material is an important consideration when selecting suitable ingredients. Shelf stability refers to the ability of the finished product to resist degradation during normal storage conditions. For example, for products comprising isocyanate functional polyurethane prepolymers such standard storage conditions would include storage in a moisture free environment at 25° C. The shelf stability of a casting material preferably exceeds 1 year when stored at ambient temperature (i.e., 25° C.), more preferably the shelf stability exceeds 3 years, and most preferably the shelf stability exceeds 5 years. The shelf stability of a casting material containing a curable resin may also be tested at elevated temperature (49° C.) to predict ambient temperature stability. Preferred casting materials withstand four weeks at 49° C., more preferred casting materials withstand eight weeks at 49° C., and most preferred casting materials withstand twelve weeks at 49° C.

Notably, many commercially available fillers, such as glass bubbles, are basic in nature (i.e., alkali) and may cause undesirable side-reactions in isocyanate functional polyurethane prepolymers. These side reactions may cause the resin to harden prematurely or prevent hardening at all. Preferred optional fillers are chosen so as to not upset the shelf stability of the resin material. When isocyanate functional polyurethane prepolymers systems are employed it is beneficial to ensure that the optional fillers are neither basic in nature nor contain basic impurities. Such basicity can result in side reactions (such as trimerization, allophonate formation, and biuret formation) with the isocyanate functional resin system which may limit the shelf stability of the product. Adverse effects of the basicity of the filler may be minimized by washing and/or neutralizing the filler with a suitable acid or by addition of an acid stabilizer to the resin.

Resin systems may also be colored for decorative purposes using dyes or pigments or both. Luminescent pigments may also be employed. Furthermore, one may alternatively wrap the splint or cast of the present invention with a decorative or informative sheet comprising raised lettering and/or figures which is capable of leaving impressions in the material. Furthermore, the materials of the present invention may be printed using suitable dyes or pigments by direct or indirect printing methods such as transfer printing, pigment printing, or ink jet printing.

Color conveniently may be used to delineate the "soft region" from the "reinforced region." For example, the reinforcement compound may contain an ingredient (e.g., a pigment or dye) that forms or exhibits a distinctive color when placed adjacent the casting material. In either way the resulting different colors may facilitate placement of the reinforcement compound where desired.

A fugitive water soluble web, such as are described in U.S. patent application Ser. No. 08/404,242, the disclosure of which is herein incorporated by reference, may be employed as a liner which separates adjacent layers of the tape (e.g., when the tape is provided as a roll).

The reinforcement compound of the present invention preferably comprises a hardenable liquid resin system. More preferably, the hardenable resin system comprises a free-radically or cationically curable or cross-linkable monomer, oligomer, or polymer. Preferred reinforcement compounds comprise one or more polymerizable substances. Addition polymerizable substances (e.g., vinyl compounds such as acrylates and methacrylates) are especially preferred. The reinforcement compound preferably can also contain appropriate polymerization catalysts (or one portion of an appropriate multi-portion catalyst system) to assist in hardening the reinforcement compound. The reinforcement compound preferably can also contain appropriate fillers, thickeners, colorants, etc.

In one embodiment, the reinforcement compound comprises a vinyl based resin system containing a redox catalyst (i.e., one portion of a two portion initiator system) that when applied to a flexible orthopedic casting tape containing a redox activator (i.e., the other portion of the two portion initiator system) causes the selected areas of the tape to set to a rigid state. The vinylic reinforcement compound may be painted on as a liquid, applied as a gel or paste out of a tube or syringe, or may be dispensed as a gel or foam out of a pressurized can. Inclusion of the redox activator in the casting tape resin provides a choice for the applier to either use the flexible casting tape in the ordinary way, i.e., without applying the vinylic compound to selected areas, or to selectively reinforce the casting tape by applying the vinylic compound to the surface of the tape. This system is desirable because no premixing of the reinforcement system is required.

In another embodiment, the reinforcement compound comprises a two-part vinyl based resin system that is mixed together, e.g., using an appropriate mixer such as a static mixer, prior to being applied to the casting tape. A combination of both systems can be used.

Suitable polymerizable components for use in the present reinforcement compound include in principle any type of vinylic compound. Suitable monomeric compounds include epoxies and esters of acrylic and methacrylic acid. Preferred monomeric compounds include methacrylates.

Lower functionality monomethacrylates including alkyl-, unsaturated alkyl-, cycloalkyl-, aryl-, hydroxyalkyl-, alkoxyalkyl-, oxiranyl-, and aminoalkyl methacrylates are somewhat useful. Higher functionality di-, tri-, tetra-, penta- and hexa-methacrylate are more preferable. Especially useful are the glycol dimethacrylates including methylene-, ethylene-, diethylene-, triethylene-, and C4-C10 polyethylene-, and propanediol- to decanediol dimethacrylates, and specialty dimethacrylates such as urethane dimethacrylate and bisphenolglycidyl dimethacrylate. Oligomeric and polymeric vinylic compounds (such as urethane and epoxy acrylates) may also be useful, particularly in combinations with one or more of the monomeric methacrylates mentioned above.

Suitable monomers, oligomers, and polymers for use in the reinforcement compound of the present invention include 2-hydroxyethylacrylate, 2-hydroxyethylmethacrylate ("HEMA"), 2- and 3-hydroxypropylacrylate, 2- and 3-hydroxypropylmethacrylate, 1,3- and 2,3-dihydroxypropylacrylate, 1,3- and 2,3-dihydroxypropylmethacrylate, 2-hydroxypropyl-1,3-diacrylate, 2-hydroxypropyl-1,3-dimethacrylate, 3-hydroxypropyl-1,2-diacrylate, 3-hydroxypropyl-1,2-dimethylacrylate, pentaerythritol diacrylate, pentaerythritol dimethacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide, 2-hydroxyethylmethacrylamide, N,N-bis(2-hydroxyethyl)acrylamide, N,N-bis(2-hydroxyethyl)methacrylamide, N-alkyl-N-hydroxyethylacrylamides, N-alkyl-N-hydroxyethylmethacrylamides, 2- and 3-hydroxypropylacrylamide, 2- and 3-hydroxypropylmethacrylamide, methacrylamidopropyltrimethylammonium chloride, polyethyleneglycol diacrylate, polyethyleneglycol dimethacrylate, glycerol dimethacrylate, glycerol diacrylate, gylcerol monomethacrylate, gylcerol monoacrylate, pentaerylthritoltrimethacrylate, pentaerylthritoltriacrylate, tetrahydrofurfural methacrylate, glyceryl-1,3-dimethacrylate, triethyleneglycol dimethacrylate, ethyl methacrylate, n-hexyl methacrylate, polyethyleneglycol dimethacrylate ("PEGDMA"), 1,6-hexanediol dimethacrylate, the dimethacrylate derived from the reaction between methacrylic acid and the diglycidyl ether of bisphenol A ("Bis-GMA"), and mixtures thereof. Preferred are 4–30 mole ethoxylated bisphenol A dimethacrylate esters. It is expected that where an acrylate monomer is suitable the methacrylate analog will likewise be suitable.

A particularly preferred mixture of monomers is obtained by combining (1) a monomer such as Bis-GMA or 4 mole bisphenol A dimethacrylate ester (e.g., CD 540 obtained from Sartomer) with (2) a monomer such as triethyleneglycol dimethacrylate.

Polymerization catalysts that can be included in the reinforcement compound and/or in the casting tape are autocure or light cure catalysts (i.e., catalysts which are sensitive to actinic radiation such as visible light) such as those mentioned in columns 28 and 29 of U.S. Pat. No. 4,539,382 and those mentioned in U.S. Pat. No. 5,154,762, chromophore-substituted halomethyl-s-triazines such as those shown in U.S. Pat. No. 3,954,475, chromophore-substituted halomethyl-oxadiozoles such as those shown in U.S. Pat. No. 4,212,970, and aryliodonium salts such as those shown in U.S. Pat. No. 5,545,676, the disclosures of which are herein incorporated by reference.

In one embodiment, the present invention describes a system consisting of a polymerizable compound that when subjected to a free radical initiator sets to a rigid material. The radical initiator is preferably formed from the reaction between an oxidizing and a reducing component of a redox pair upon physical contact. In an alternative embodiment the redox process is coupled to a visible light cure mechanism, or alternatively is completely replaced by a visible light cure process.

The use of redox pairs to generate the free radical initiator is an entirely chemical reaction dependent process. Preferably, the active reducing component of the redox system is mixed into the polyurethane based resin of the casting tape, and the polymerizable component and the oxidizing redox component are mixed into a formulation to be dispensed onto the casting tape.

In an alternative setting the two redox components are both included in the delivery system and are dispensed out of a twin screw or plunger type dispenser. In an optimal setting a combination of the alternatives is used, i.e., the combined effect of catalyst in the dispensed medium and additional catalyst effect from the surrounding casting tape provide a quick and thorough setting at the surface of the dispensed medium, with a slower progressive setting at the core of the dispensed medium. The advantage of this system would be a higher degree of control of the set profile.

Suitable reducing agents or activators include: inorganic reducing components such as, ferrous sulphate, sodium sulphite, sodium dithionite, sodium thiosulphate, ferrous chloride, sodium metabisulphite, or organic salts like sodium formaldehyde sulphoxylate as discussed in Potter et al. (U.S. Pat. No. 4,672,956). The presently most preferred reducing components or activators are selected among the group of amines. Tertiary amines are most preferred in order to optimize miscibility with the nonaqueous polyurethane resin. Primary and secondary amines are presently less preferred for use with isocyanate resin systems as the reactive N-bound hydrogen(s) may react with the isocyanate groups in the curable-resin and thus elicit a change in the characteristics of the casting tape, most prominently shortening the shelf life. In theory, the oxidizing component might be mixed into the resin instead of the amine, however, typical casting resins already make use of a tertiary amine for catalyzing the isocyanate reaction, and although these amines are fairly slowly reacting with the redox oxidizer, considerable reduction in shelf life is anticipated.

The redox activity of the amines has been found to depend on the stability of the selected amines, i.e., the ability to delocalize the electrons on nitrogen throughout the molecule. Thus, amines with conjugated double bond systems, especially in aromatic ring systems, are presently found to be the most suitable. Also, the degree of electron donating or accepting substituents on the aromatic ring, as well as the steric properties of the N-substituents are believed to be prominent determinators of the redox activity. Further, the basicity of the amine may greatly influence the shelf life of the isocyanate resin, as the polyurethane formation is typically base catalyzed. Thus, the lower the pKa of the base, the longer the shelf life. It has been found that amines having a pKa well below 8 are most suitable.

Suitable amines include N,N-disubstituted anilines such as N,N-dimethylaniline and N,N-diethylaniline, and phenyl substituted anilines such as 4-tert-butyl-N,N-dimethylaniline. More suitable are N,N-disubstituted toluidines such as N,N-dimethyl-para-toluidine or N,N-diethyl-para-toluidine or corresponding meta-toluidines, and even more so tetra- and eventually penta-substituted anilines such as N,N-3,5-tetramethylaniline and N,N-2,4,6 pentamethylaniline. Optionally, the substituents may contain functional groups such as —OH, as in N-ethyl anilino ethanol, N-ethyl-toluidino ethanol, N,N-dihydroxyethylaniline or N,N-dihydroxyethyl toluidine, and di-(2-hydroxy) propyl aniline or di-(2-hydroxy) propyl toluidine. It has been noted, though, that the incorporation of hydroxyl groups tends to decrease the redox reactivity, possibly because of a restrictive binding of the catalyst to the isocyanate, and further that the disubstituted hydroxyl compounds tend to shorten the shelf life of the isocyanate resin. Cyclic ethers like N-substituted morpholines or N-substituted dimorpholines may be suitable, preferably when the substituents are small. Other heterocyclic amines might prove suitable. Potentially suitable are disubstituted naphthyl amine and anthracyl amine, tetrasubstituted benzidine, and heterocyclic compounds like N-substituted pyrrol, pyrazole, and imidazol, as well as pyridine, pyridazine, pyrimidine, pyrazine, triazine, indole, quinoline, isoquinoline, and purine.

The activator or reducing agent of the redox system is preferably chosen among suitable tertiary amines and is mixed into the casting resin in an amount allowing appropriate set characteristics and work time after being activated. Without redox activation the tertiary amine should impart no or negligible adverse effects to the features of the casting tape. The amount of tertiary amine activator mixed into the casting resin should be sufficient to assist in the initiation of the cure of the reinforcement composition so that the treated area is significantly hardened to form a reinforced casting article. Suitable amine concentrations are 0.02–0.2% (w/w) in the methacrylate composition, and 0.2–2.0% (w/w) in the casting tape resin.

The redox catalyst or oxidizing agent is preferably chosen among suitable organic peroxides and is preferably mixed into or dissolved into the liquid solution of suitable vinyl compounds, preferably methacrylate esters.

Suitable redox catalysts are organic dialkyl or diacyl peroxides such as t-butylperoxy pivalate, 2,4-dichlorobenzoyl peroxide, caprylyl peroxide, lauroyl peroxide, acetyl peroxide, t-butyl peroxyisobutyrate, benzoyl peroxide, p-chlorobenzoyl peroxide, hydroxyheptyl peroxide. cyclohexanone peroxide, t-butyl peracetate, t-butylperoxy isopropyl carbonate, t-butyl perbenzoate, dicumyl peroxide, methyl ethyl ketone peroxide, di-t-butyl peroxide, and bis-4-t-butylcyclohexyl peroxy dicarbonate. Most preferred are diacyl peroxides such as (di)benzoyl peroxide. Preferably the catalyst should amount to 0.2–2.0% of the reinforcing composition (w/w).

When the casting tape comprises a water-curable resin such as an isocyanate based prepolymer, the requirement of a non-aqueous storage environment limits the usefulness of oxidizers belonging to the group of persalts (e.g., ammonium persulfate, potassium persulfate, and potassium permanganate), ferric (III) and cobalt (III) salts (e.g., ferric (III) chloride and cobalt (III) chloride), and copper (II) salts (e.g., copper (II) sulphate, or the more controllable Cu (II) acetylacetonate). Also, hydroperoxides, mainly the lower molecular weight types, are less desirable based on reactivity/stability considerations.

The reinforcement compound may be applied on top of the casting tape, or between layers aiming to penetrate the layers to a degree that provides optimal strength, while preferably not bleeding through to the underlayment.

In the most preferred clinical setting, the cast technician wraps one to three layers of casting tape, holds the remainder of the roll in one hand while dispensing a suitable amount of reinforcement compound onto the desired area of the cast, and finishes the wrapping of the cast. Depending on skill level, the casting tape may be pre-activated by dipping in water, or not.

The dispensable reinforcement compound preferably comprises a polymerizable component, a catalyst and optional fillers, fragrants and stabilizers. In one setting the reinforcing compound may be dispensed as a cream or paste out of a tube or bottle, or be mixed with a suitable propellant and dispensed as a thick lather out of a pressurized can. In different settings the composition is impregnated into or onto a carrier scrim and is dispensed as a tape formulation, or the composition is extruded into a preferably flexible web to be dispensed like a tape. In another embodiment the dispenser is a double-barreled syringe type or twin screw device supplied with a mixing head such as a single-use disposable static mixing tip. These systems would all be reusable. In a different setting a disposable pouch containing a metered dose of methacrylate composition may provide a disposable delivery system. In a particular setting the pouch would consist of two compartments separated by a seam that would rupture when mechanically crunching the pouch, allowing for mixing of the two parts.

Methacrylic acid and its esters are readily polymerizable and generally must be stabilized to prevent premature reactions. Potential stabilizers during preparation and storage are phenothiazine, hydroquinone (HQ), tert-butyl hydroquinone, and methoxy hydroquinone (MEHQ). Other stabilizers to prevent peroxide initiated polymerization include 2,6-di-t-butyl cresol (butylated hydroxytoluene (BHT), butylated hydroxyanisole (methoxyphenol), and tert-butyl catechol. Levels of stabilizers generally are less than 100 ppm for the quinones, and less than 1 weight percent for the other stabilizers.

The composition may also contain a thickening agent to assist in controlling consistency. This is particularly important to prevent the composition applied between 2–6 layers of casting tape from protruding to either of the surfaces of the casting tape and thus present a sticky or hazardous component to the patient and to the applier. The thickening agent is preferably inert and not reactive with the other ingredients in the formulation. Typical thickening agents that are useful include cosmetic grade talc, various types of silica compounds, calcium carbonate variations, and organic polymer powders such as polymethylmethacrylate, aryl ureas such as naphthyl urea and indanthrene. The preferred thickener is talc in an amount of 10–50% w/w.

Optionally, fillers may be incorporated that enhance strength. Useful fillers include, but are not limited to ground glass, glass fibers, glass bubbles, glass microspheres or mixtures of these materials, wood fibers, and particles of polymers such as polyethylene and polypropylene. The preferred strengthener is a Nyad G material (treated or untreated calcium metasilicate) in an amount of 10–50% w/w. Additionally various types of fragrances in amounts sufficient to achieve the desired effect may be used.

It may be desirable to include a colorant in the reinforcing composition in order to guide the applier as to the correct positioning of the reinforcement, as well as indicating the area less desirable for cutting during removal of the cast. Colorants may be inorganic pigments, organic pigments, and dyes. Colorants may be mixed physically into the vinylic based reinforcement composition, or may be functionalized with a vinyl group and subsequently copolymerized with the composition.

EXAMPLES

The following examples are offered to aid in understanding of the present invention and are not to be construed as limiting the scope thereof. Unless otherwise indicated, all parts and percentages are by weight.

Example 1

Reinforced Casting Articles

The feasibility of reinforcing a casting tape having a curable resin that contains an activator which initiates the hardening of an addition polymerizable reinforcement composition was demonstrated in this example.

A liquid isocyanate-terminated polyurethane prepolymer resin ("Resin-1A") was prepared by combining the ingredients listed in Table 1a.

TABLE 1a

"Resin-1A"[1]

| Ingredient | Parts (by weight) |
| --- | --- |
| ISONATE 2143L (Dow Chemical) | 20.39 |
| Polyol ARCOL LHT-28 (ARCO Chemical) | 29.90 |
| Polyol ARCOL LHT-42 (ARCO Chemical) | 44.41 |
| Pluronic F-108 (BASF) | 3.56 |
| DMDEE (2,2'-Dimorpholinodiethyl Ether) (Huntsman Chemical, Austin, TX) | 1.00 |
| BHT (Butylated Hydroxytoluene) (PMC Specialty Group, Redlands, CA) | 0.49 |
| Antifoam 1400 (Dow Chemical) | 0.18 |
| p-Toluenesulfonyl Chloride (AKZO Chemical) | 0.05 |

[1]The combined ingredients provide an NCO to OH ratio of 3.0

An activator (DMT) which participated in the hardening of a separate reinforcement composition was added to "Resin-1A" to give "Resin-1B" as described in Table 1b.

TABLE 1b

"Resin-1B"

| Ingredient | Parts (by weight) |
| --- | --- |
| "Resin-1A" (Table 1a) | 99.0 |
| DMT (N,N'-Dimethyl-p-toluidine) (Aldrich Chemical) | 1.0 |

A fiberglass fabric was knit according to the process described in U.S. Pat. No. 4,609,578, which is herein incorporated by reference. The fiberglass fabric was 5 cm wide (2 inches) and had 41 wales of ECDE 75 1/0 fiberglass yarn.

Sample casting tapes were made by coating the fiberglass fabric with "Resin-1B" at a coating weight of 39%. The sample casting tapes were designed to form soft, flexible, orthopedic casting articles when cured.

A reinforcement composition ("RC-1C") was prepared by combining the ingredients listed in Table 1c.

TABLE 1c

Reinforcement Composition "RC-1C"

| Ingredient | Parts (by weight) |
| --- | --- |
| Bis-GMA (Bisphenol A Diglycidyl Ether Dimethacrylate) | 69 |
| TEGDMA (Triethylene Glycol Dimethacrylate) | 29 |
| BPO (Benzoyl Peroxide) (Aldrich Chemical) | 2 |

Reinforced casting articles were prepared by either kneading the reinforcement composition into the casting tape or by smearing the reinforcement composition onto the surface of the casting tape. Coating weights in both cases were 44%.

Control samples were prepared from 6 layers of the aforementioned fiberglass fabric coated with "Resin-1A" and reinforced with 3 layers of SCOTCHCAST PLUS Tape (3M Company), a conventional resin-treated fiberglass tape designed to form a rigid orthopedic support device when cured. Additional control samples were prepared from the fiberglass fabric coated with "Resin-1A" or with "Resin-1B". None of the control samples were treated with a reinforcement composition. Six-layer laminates of the reinforced casting articles and the control samples were tested for lamination strength according to the following test method:

Lamination Strength Test Method

This test measured the force (lamination strength) necessary to resist deflection of reinforced, laminated casting articles and control (nonreinforced) casting articles within the scope of the present invention. The basic method was as follows:

The reinforcement compositions were applied to approximately 5×120 cm pieces of resin-containing casting tape by one of the following three techniques:

1) kneading onto the surface of the tape,
2) smearing onto the surface of the tape, or
3) smearing between layers three and four of the laminate.

The casting tape was folded into six layers on top of each other to provide an approximate 20-cm long laminate. The laminate was immediately dipped into room temperature water for 30 seconds, and then placed between two sheets of polyethylene film. A 15×20 cm load of 1537 g was placed on top of the laminate in the cross direction, but without putting any additional pressure on the sample. The laminate was trimmed to a length of 15 cm and the load was removed after 30 seconds. The polyethylene film was removed after either 8 minutes, 15 minutes, 30 minutes, or 24 hours dwelling ("dwell time"), and the flat laminate was placed in the fixture of a commercial Instron testing instrument. The laminate was centered across two bottom cylinders (13.4 cm long, 1.9 cm diameter) supported on 12-cm high blocks and spaced 7.5 cm apart. A third cylinder of the exact same dimensions was attached to the fixture of the movable part of the Instron testing instrument and centered between the lower cylinders. The third cylinder was brought down to deflect the flat laminate at a speed of 5 cm/minute. The peak forces ("lamination strengths") to deflect each sample were recorded.

Lamination strengths of the reinforced casting articles are compared to control samples after 8 min, 30 min, and 24 hr dwell times as provided in Table 1d.

TABLE 1d

"Reinforced Casting Articles"

| Run # | Method of Applying the Reinforcement Composition (RC) "RC-1C" to the Casting Tape Containing "Resin-1B" | Lamination Strength (N/cm width) | | |
|---|---|---|---|---|
| | | 8 min. | 30 min. | 24 hrs. |
| 1 | Kneading | 10.78 | 15.98 | 20.80 |
| 2 | Smearing onto the surface | 8.32 | 10.81 | 12.51 |
| C3 | Control (No RC Applied) Casting Tape with "Resin 1A" plus "SCOTCHCAST" Tape Reinforcement | 4.70 | 6.69 | 15.49 |
| C4 | Control (No RC Applied) Casting Tape with "Resin 1A" | 1.40 | 1.66 | 2.63 |

TABLE 1d-continued

"Reinforced Casting Articles"

| Run # | Method of Applying the Reinforcement Composition (RC) "RC-1C" to the Casting Tape Containing "Resin-1B" | Lamination Strength (N/cm width) | | |
|---|---|---|---|---|
| | | 8 min. | 30 min. | 24 hrs. |
| C5 | Control (No RC Applied) Casting Tape with "Resin 1B" | 1.89 | 1.82 | 1.84 |

It is concluded from this example that reinforced casting articles having the greatest strength were obtained by kneading the reinforcement composition into the fiberglass fabric containing the curable prepolymer resin (Run 1). However, more than adequate strength resulted when the reinforcement composition was simply smeared onto the treated fabric (Run 2). Also, both of the reinforced casting articles were much stronger than the nonreinforced control samples which had not been treated with any reinforcement composition (Runs C4 and C5).

Example 2

Reinforced Casting Articles

The effects of utilizing alternative vinylic compounds as polymerizable components of the reinforcement compositions were evaluated in this example.

Alternative reinforcement compositions ("RC-2A" through "RC-2F") were prepared by combining the ingredients listed in Table 2a.

TABLE 2a

Reinforcement Compositions

| Name | Ingredient | Parts (by weight) |
|---|---|---|
| "RC-2A" | Dipentaerythritol Penta-/hexa-acrylate (Aldrich Chemical) | 69 |
| | TEGDMA | 29 |
| | BPO | 2 |
| "RC-2B" | Bis-GMA | 69 |
| | TMPTMA (Trimethylol Propane Trimethacrylate) (Rohm Tech, Inc.) | 29 |
| | BPO | 2 |
| "RC-2C" | Bis-GMA | 69 |
| | PEGDMA [Poly(ethyleneglycol-400) Dimethacrylate] (Aldrich Chemical) | 29 |
| | BPO | 2 |
| "RC-2D" | Bis-GMA | 69 |
| | ETOX (4-Mole Ethoxylated Bisphenol-A Dimethacrylate) (CD 540, Sartomer Co.) | 29 |
| | BPO | 2 |
| "RC-2E" | Bis-GMA | 49 |
| | ETOX | 49 |
| | BPO | 2 |
| "RC-2F" | Bis-GMA | 29 |
| | ETOX | 69 |
| | BPO | 2 |

Reinforced casting articles were prepared by smearing the reinforcement composition onto the surface of the casting tape containing "Resin-1B" as described in Example 1. Lamination strengths of the reinforced casting articles utilizing various vinylic compounds are listed in Table 2b.

TABLE 2b

"Reinforced Casting Articles"

| Run # | Reinforcement Composition Applied to Casting Tape Containing "Resin-1B" | Lamination Strength (N/cm width) | | |
|---|---|---|---|---|
| | | 8 min. | 30 min. | 24 hrs. |
| 1 | "RC-2A" | 5.54 | 7.05 | 8.36 |
| 2 | "RC-2B" | 3.68 | 5.78 | 8.03 |
| 3 | "RC-2C" | 6.03 | 9.10 | 11.97 |
| 4 | "RC-2D" | — | 9.11 | 10.86 |
| 5 | "RC-2E" | — | 10.34 | 12.09 |
| 6 | "RC-2F" | — | 7.18 | 16.82 |
| Table 1d Run 2 | "RC-1C" (Table 1c) | 8.32 | 10.81 | 12.51 |
| Table 1d Run C5 | Control (No RC Applied) | 1.89 | 1.82 | 1.84 |

All of the reinforced casting articles of this example were much stronger than the control sample which was not treated with a reinforcement composition. Most effective vinylic compound mixtures were combinations of Bis-GMA with PEGDMA (Run 3), with ETOX (Runs 4, 5, and 6), and with TEGDMA (Example 1, Table 1d, Run 2).

Example 3

Reinforced Casting Articles

The effects of utilizing alternative redox catalysts (or oxidizing agents) in the reinforcement compositions were evaluated in this example.

The alternate reinforcement composition ("RC-3A") was prepared by combining the ingredients listed in Table 3a.

TABLE 3a

Reinforcement Composition "RC-3A"

| Ingredient | Parts (by weight) |
|---|---|
| Bis-GMA | 69 |
| TEGDMA | 29 |
| Cumene Peroxide (Aldrich Chemical) | 2 |

Reinforced casting articles were prepared by smearing the reinforcement compositions onto the surface of the casting tapes prepared from "Resin-1B" as described in Example 1. Lamination strengths of reinforced casting articles made from "RC-3A" (containing cumene peroxide catalyst) were compared to articles made from "RC-1C" (containing benzoyl peroxide catalyst) as listed in Table 3b.

TABLE 3b

"Reinforced Casting Articles"

| Run # | Reinforcement Composition Applied to Casting Tape Containing "Resin-1B" | Lamination Strength (N/cm width) | | |
|---|---|---|---|---|
| | | 8 min. | 30 min. | 24 hrs. |
| 1 | "RC-3A" (Table 3a) | 1.93 | 2.10 | 2.45 |
| Table 1d Run 2 | "RC-1C" (Table 1c) | 8.32 | 10.81 | 12.51 |
| Table 1d Run C5 | Control (No RC Applied) | 1.89 | 1.82 | 1.84 |

In this example, both reinforced casting articles had increased strength over the control sample (no reinforcement composition added). However, benzoyl peroxide appeared to be much more effective than cumene peroxide as a redox catalyst in the reinforcement composition.

Example 4

Reinforced Casting Articles

The effects of varying the concentrations of the tertiary amine activators in the curable resins and of the redox catalyst in the reinforcement compositions were evaluated in this example.

Isocyanate-terminated prepolymer resins were prepared by adding to "Resin-1A" (Example 1) either activator DMT or TBDMA (4-tert-Butyl-N,N-dimethylaniline, Aldrich Chemical) at various concentration levels (1.0%, 1.5%, or 2.0%). Sample casting tapes were made by coating fiberglass fabric with the various prepolymer resins as described in Example 1. Reinforcement compositions were prepared as described for "RC-1C" (Example 1), except that the BPO redox catalyst was added at various concentration levels (1.0%, 1.5%, or 2.0%). Reinforced casting articles were prepared by kneading the various reinforcement compositions into the casting tapes as described in Example 1. Lamination strengths (after 24 hr dwell time) of the reinforced casting articles prepared from the various sample casting tapes and the various reinforcement compositions of this example are listed in Table 4a.

TABLE 4a

"Reinforced Casting Articles"

| Run # | Activator Concentration in Prepolymer Resin "Resin-1A"(Table 1a) | | Catalyst Concentration in Reinforcement Composition "RC-1C" (Table 1c) | | Lamination Strength (N/cm width) |
|---|---|---|---|---|---|
| | Activator | Weight % | Catalyst | Weight % | 24 hrs. |
| 1 | DMT | 1.0 | BPO | 1.0 | 13.62 |
| 2 | DMT | 1.0 | BPO | 1.5 | 20.07 |
| 3 | DMT | 1.0 | BPO | 2.0 | 29.01 |
| 4 | DMT | 1.5 | BPO | 1.0 | 13.81 |
| 5 | DMT | 1.5 | BPO | 1.5 | 10.18 |
| 6 | DMT | 1.5 | BPO | 2.0 | 20.23 |
| 7 | DMT | 2.0 | BPO | 1.0 | 19.17 |
| 8 | DMT | 2.0 | BPO | 1.5 | 16.61 |
| 9 | DMT | 2.0 | BPO | 2.0 | 14.79 |
| 10 | TBDMA | 1.0 | BPO | 1.0 | 2.49 |
| 11 | TBDMA | 1.0 | BPO | 1.5 | 10.41 |
| 12 | TBDMA | 1.0 | BPO | 2.0 | 20.37 |
| 13 | TBDMA | 1.5 | BPO | 1.0 | 9.48 |
| 14 | TBDMA | 1.5 | BPO | 1.5 | 8.31 |
| 15 | TBDMA | 1.5 | BPO | 2.0 | 24.54 |
| 16 | TBDMA | 2.0 | BPO | 1.0 | 15.02 |
| 17 | TBDMA | 2.0 | BPO | 1.5 | 18.88 |
| 18 | TBDMA | 2.0 | BPO | 2.0 | 17.93 |
| Table 1d Run C5 | DMT | 1.0 | Control Sample (No RC Applied) | | 1.84 |

All of the reinforced casting articles from this example had increased lamination strength compared to the control sample. Utilization of 1.0% DMT tertiary amine activator and 2.0% BPO redox catalyst appears to be the optimal combination from this example.

Example 5

Reinforced Casting Articles

The effects of utilizing alternative tertiary amine activators in the isocyanate-terminated prepolymer resin were evaluated in this example.

Alternate tertiary amine activators were added to "Resin-1A" (Example 1) to give the alternate resins ("Resin-5A", "Resin-5B", "Resin-5C", "Resin-5D", and "Resin-5E") as listed in Table 5a.

TABLE 5a

Prepolymer Resins

| Name | Ingredient | Parts (by weight) |
|---|---|---|
| "Resin-5A" | "Resin-1A" (Table 1a) | 99.0 |
|  | TBDMA (4-tert-Butyl-N,N-dimethylaniline) | 1.0 |
| "Resin-5B" | "Resin-1A" | 99.0 |
|  | DHEPT (N,N-Dihydroxyethyl-p-toluidine) (3M Dental Division) | 1.0 |
| "Resin-5C" | "Resin-1A" | 99.0 |
|  | DMAPE[4-(Dimethylamino)phenethyl Alcohol] (Eastman Kodak) | 1.0 |
| "Resin-5D" | "Resin-1A" | 99.0 |
|  | ETE [2-(N-Ethyl-toluidino) Ethanol] (Aldrich) | 1.0 |
| "Resin-5E" | "Resin-1A" | 99.0 |
|  | TMA (N,N,3,5-Tetramethylaniline) (Aldrich) | 1.0 |

Reinforced casting articles were prepared by applying the reinforcement composition ("RC-1C", Example 1, Table 1c) to fiberglass casting tapes prepared from prepolymer resins "Resin-1B", "Resin-5A"and "Resin-5B"(kneading method described in Example 1) and from resins "Resin-1B", "Resin-5C") "Resin-5D") and "Resin-5E" (smearing method described in Example 1). Lamination strengths of the reinforced casting articles made from prepolymer resins containing different tertiary amine activators are compared to control samples as listed in Table 5b.

TABLE 5b

"Reinforced Casting Articles"

| Run # | Prepolymer Resin (Activator) | Method of Applying the Reinforcement Composition "RC-1C" to the Casting Tape | Lamination Strength (N/cm width) 30 min. | 24 hrs. |
|---|---|---|---|---|
| Table 4a Run 12 | "Resin-5A" (Table 5a) (TBDMA) | Kneading | — | 20.37 |
| 1 | "Resin-5B" (Table 5a) (DHEPT) | Kneading | — | 2.45 |
| Table 4a Run 3 | "Resin-1B" (Table 1b) (DMT) | Kneading | — | 29.01 |
| 2 | "Resin-5C" (Table 5a) (DMAPE) | Smearing on Surface | 3.01 | — |
| 3 | "Resin-5D" (Table 5a) (ETE) | Smearing on Surface | 2.46 | 12.28 |
| 4 | "Resin-5E" (Table 5a) (TMA) | Smearing on Surface | 19.46 | 22.96 |
| Table 1d Run 2 | "Resin-1B" (Table 1b) (DMT) | Smearing on Surface | 10.81 | 12.51 |
| Table 1d Run C5 | "Resin-1B" (Table 1b) (DMT) | Control (No RC Applied) | 1.82 | 1.84 |

In this example, all of the tertiary amines were effective activators in providing reinforced casting articles stronger than the control samples. When the reinforcement composition was applied by the smearing method, articles of greatest strength resulted when either ETE, TMA, or DMT was utilized as the tertiary amine activator.

Example 6

Reinforced Casting Articles

The effect of varying the coating weight of the reinforcement composition on the casting tapes was evaluated in this example.

Reinforced casting articles were prepared by smearing the reinforcement composition "RC-1C" onto the casting tape prepared from "Resin-1B" as described in Example 1, except that the coating weight was increased from 44% to 54%. Lamination strengths of the reinforced casting articles prepared at the different coating weights are compared in Table 6a.

TABLE 6a

"Reinforced Casting Articles"

| Run # | Coating Weight of Reinforcement Composition "RC-1C" on Casting Tapes made from "Resin-1B" | Lamination Strength (N/cm width) | | |
|---|---|---|---|---|
|  |  | 8 min. | 30 min. | 24 hrs. |
| 1 | 54% | 9.29 | 15.95 | 19.45 |
| Table 1d Run 2 | 44% | 8.32 | 10.81 | 12.51 |

It is concluded from this example that increasing the coating weight of reinforcement composition on the prepolymer resin-treated casting tape can result in reinforced casting articles of increased lamination strength.

Example 7

Reinforced Casting Articles

The effects of adding varying concentrations of silica filler to various reinforcement compositions were evaluated in this example.

Reinforcement compositions with added silica filler ("RC-7A", "RC-7B", and "RC-7C") were prepared by combining the ingredients listed in Table 7a. Reinforced casting articles were prepared by smearing these reinforcement compositions onto casting tapes prepared from "Resin-1B" as described in Example 1. Lamination strengths of the resulting reinforced casting articles containing silica filler and of the reinforced casting article containing no filler (Example 1) are compared in Table 7a.

TABLE 7a

"Reinforced Casting Articles"

| Run # | Reinforcement Composition Applied to Casting Tape Containing "Resin-1B" | | | Lamination Strength (N/cm width) | | |
|---|---|---|---|---|---|---|
|  | Name | Ingredient | Parts (By Wt.) | 8 min. | 30 min. | 24 hrs. |
| 1 | "RC-7A" | Bis-GMA | 67 | 7.71 | 11.39 | 14.20 |
|  |  | TEGDMA | 29 |  |  |  |
|  |  | BPO | 2 |  |  |  |
|  |  | Silica Filler CABOSIL TS-720 (Cabot Corp) | 2 |  |  |  |
| 2 | "RC-7B" | Bis-GMA | 65 | 3.51 | 4.73 | 6.13 |
|  |  | TEGDMA | 28 |  |  |  |
|  |  | BPO | 2 |  |  |  |

TABLE 7a-continued

"Reinforced Casting Articles"

| Run # | Name | Reinforcement Composition Applied to Casting Tape Containing "Resin-1B" | | Lamination Strength (N/cm width) | | |
|---|---|---|---|---|---|---|
| | | Ingredient | Parts (By Wt.) | 8 min. | 30 min. | 24 hrs. |
| 3 | "RC-7C" | Silica Filler | 5 | 3.51 | 6.48 | 7.36 |
| | | Bis-GMA | 46.5 | | | |
| | | TEGDMA | 46.5 | | | |
| | | BPO | 2 | | | |
| Table 1d Run 2 | "RC-1C" | Silica Filler | 5 | 8.32 | 10.81 | 12.51 |
| | | Bis-GMA | 69 | | | |
| | | TEGDMA | 29 | | | |
| | | BPO | 2 | | | |
| Table 1d Run C5 | Control (No RC Applied) | Silica Filler | 0 | 1.89 | 1.82 | 1.84 |

Silica filler was added to the reinforcement compositions in order to increase viscosity and thereby make the compositions more suitable for a variety of practical dispensing systems. Adding 2% silica filler to the reinforcement composition "RC-1C" produced a more viscous, but still readily flowable composition. The addition of 5% silica filler provided a paste-like material. The testing results from this example showed that all of the reinforced casting articles had significantly enhanced lamination strengths compared to the control sample (no reinforcement composition added). However, less hardening of the casting articles was achieved at the higher concentration (5%) of added silica filler.

Example 8

Reinforced Casting Articles

The prepolymer "Resin-1A" (Table 1a, Example 1) contains the tertiary amine, 2,2'-Dimorpholinodiethyl Ether (DMDEE). The purpose of this example was to evaluate whether DMDEE alone, without the addition of another tertiary amine, could be an effective activator for assisting in the cure of a polymerizable reinforcement composition.

Reinforced casting articles were prepared by smearing the reinforcement composition "RC-1C" onto a casting tape prepared from "Resin-1A" (containing 1% DMDEE) and onto a casting tape prepared from "Resin-1B" (containing 1% DMDEE and 1% DMT) as described in Example 1. Lamination strengths of the resulting reinforced casting articles are compared to control samples (no reinforcement composition added) as listed in Table 8a.

TABLE 8a

"Reinforced Casting Articles"

| Run # | Prepolymer Resin (Activator) | Reinforcement Composition | Lamination Strength (N/cm width) | | |
|---|---|---|---|---|---|
| | | | 8 min. | 30 min. | 24 hrs. |
| 1 | "Resin-1A" (DMDEE) | "RC-1C" (Table 1c) | 1.65 | 2.21 | 3.00 |
| Table 1d Run 2 | "Resin-1B" (DMDEE + DMT) | "RC-1C" | 8.32 | 10.81 | 12.51 |
| Table 1d Run C4 | "Resin-1A" (DMDEE) | Control (No RC Applied) | 1.40 | 1.66 | 2.63 |
| Table 1d | "Resin-1B" | Control | 1.89 | 1.82 | 1.84 |

TABLE 8a-continued

"Reinforced Casting Articles"

| Run # | Prepolymer Resin (Activator) | Reinforcement Composition | Lamination Strength (N/cm width) | | |
|---|---|---|---|---|---|
| | | | 8 min. | 30 min. | 24 hrs. |
| Run C5 | (DMDEE + DMT) | (No RC Applied) | | | |

It is concluded from this example that the tertiary amine DMDEE present in the prepolymer resin does not provide a significant hardening effect on the reinforced casting article compared to the control sample (Run 1 vs Run C4 of Table 1d, Example 1). In comparison, DMT is an effective activator for the reinforcement composition.

Example 9

Reinforced Casting Articles

The purpose of this example was to evaluate the effect of applying the reinforcement composition between layers of the resin-coated casting tape as compared to the top-surface application method.

Reinforced casting articles were prepared by squeezing the paste-like reinforcement composition ("RC-7B", containing 5% silica filler; Table 7a) between layers 3 and 4 ("Center Application") of the casting tape containing "Resin-1B" (Table 1b). Coating weights of 16% and 30% were utilized. Lamination strengths of the resulting reinforced casting articles are compared in Table 9a to articles previously prepared from squeezing the viscous "RC-7B" onto the surface ("Top Surface Application") of the casting tape or from smearing the more fluid "RC-1C" (Table 1c) onto the surface of the casting tape (44% coating weights).

TABLE 9a

"Reinforced Casting Articles"

| Run # | Reinforcement Composition | Reinforcement Composition Applied to Casting Tape Containing "Resin-1B" | | Lamination Strength (N/cm width) 30 min. |
|---|---|---|---|---|
| | | Application Method | Coating Weight | |
| 1 | "RC-7B" (Table 7a) | "Center" | 16% | 6.84 |
| 2 | "RC-7B" | "Center" | 30% | 10.87 |
| Table 7a Run 2 | "RC-7B" | "Top Surface" | 44% | 4.73 |
| Table 1d Run 2 | "RC-1C" (Table 1c) | "Top Surface" | 44% | 10.81 |
| Table 1d Run C5 | Control (No RC Applied) | | | 1.82 |

It is concluded from this example that the more viscous reinforcement composition (with silica filler) squeezed between the center two layers of casting tape produced reinforced casting articles of similar strength to those previously prepared by smearing the more fluid (without silica filler) reinforcement compositions on the top surface of the casting tape. This was observed even though the coating weights of the "Center Applications" were much lower than the "Top Surface Applications". All of the reinforced casting articles of this example were much stronger than the control sample (no reinforcement composition added). Additionally, it was noted that the surface tackiness and discoloration of the reinforced casting articles were far less prominent in the samples prepared using "Center Applications".

Example 10

Reinforced Casting Articles

The purpose of this example was to assess whether the addition of a light-activated compound to the vinylic, polymerizable reinforcement composition would provide an increased catalytic effect.

Reinforced casting articles were prepared by smearing the reinforcement composition "RC-1C" with and without added CPQ (camphorquinone) (0.5%) onto casting tapes prepared from prepolymer "Resin-1B" as described in Example 1, and allowed to set under room light conditions. Lamination strengths of the resulting reinforced casting articles are compared in Table 10a.

TABLE 10a

"Reinforced Casting Articles"

| | Reinforcement Composition Applied to Casting Tape Containing "Resin-1B" | | | Lamination Strength (N/cm width) |
|---|---|---|---|---|
| Run # | Reinforcement Composition | Added Compound | Weight % | 30 min. |
| 1 | "RC-1C" | CPQ (Camphorquinone) (Aldrich Chemical) | 0.5 | 14.69 |
| Table 1d Run 2 | "RC-1C" | None | | 10.81 |

The results of this experiment suggest an additive catalytic effect from the light-activated CPQ. This catalyst apparently enhanced the polymerization and resulting hardening effect of the reinforcement composition.

Example 11

Reinforced Casting Articles

The feasibility of reinforcing a casting tape containing a curable resin by applying a polymerizable reinforcement composition containing a tertiary amine activator which assists in the hardening of the reinforcement composition was demonstrated in this example. The reinforcing effect of having a tertiary amine activator in both the curable resin and the reinforcement composition was also investigated.

Alternate reinforcing compositions ("RC-11A", "RC-11B", and "RC-11C") were prepared by combining the ingredients as listed in Table 11a.

TABLE 11a

Reinforcement Compositions

| Name | Ingredient | Parts (by weight) |
|---|---|---|
| "RC-11A" | Bis-GMA | 69 |
| | ETOX | 30 |
| | BPO | 1 |
| | ETE (Activator) | 0.06 |
| "RC-11B" | Bis-GMA | 69.6 |
| | ETOX | 29.8 |
| | BPO | 0.5 |
| | ETE (Activator) | 0.06 |
| "RC-11C" | Bis-GMA | 69.6 |

TABLE 11a-continued

Reinforcement Compositions

| Name | Ingredient | Parts (by weight) |
|---|---|---|
| | ETOX | 29.8 |
| | BPO | 0.5 |

Reinforcement casting articles were prepared by smearing the reinforcement composition "RC-11A" onto the casting tape prepared from "Resin-1A" (no added DMT activator) as described in Example 1, and by smearing the reinforcement compositions "RC-11B" and "RC-11C" onto casting tapes prepared from "Resin-1B" (containing DMT activator). Lamination strengths of the resulting reinforced casting articles are compared in Table 11b.

TABLE 11b

"Reinforced Casting Articles"

| | Prepolymer Resin Coated on | Reinforcement Composition | Lamination Strength (N/cm width) | | | |
|---|---|---|---|---|---|---|
| Run # | Fiberglass Fabric | Applied to Casting Tape | 8 min | 15 min | 30 min | 24 hrs. |
| 1 | "Resin-1A" (no DMT Activator) | "RC-11A" (with ETE Activator) | 1.84 | — | 6.48 | 5.35 |
| 2 | "Resin-1B" (with DMT) | "RC-11B" (with ETE) | — | 2.89 | — | — |
| 3 | "Resin-1B" (with DMT) | "RC-11C" (no ETE) | — | 0.70 | — | — |
| Table 1d Run C4 | "Resin 1A" | Control (No RC Applied) | 1.40 | — | 1.66 | 2.63 |
| Table 1d Run C5 | "Resin 1B" | Control (No RC Applied) | 1.89 | — | 1.82 | 1.84 |

It is concluded from this example that reinforcement compositions containing a tertiary amine activator, such as ETE, can be utilized to prepare reinforced casting articles of increased strength. This was true for applications of the reinforcement composition to casting tapes containing curable resins without added DMT (Run 1) or with added DMT (Run 2) as an additional tertiary amine activator. It is also noted that the reinforcement composition "RC-11B" of this example contained a lower concentration of the redox catalyst BPO (0.5% vs the generally used 1.0%), which is advantageous from the standpoint of reinforcement composition shelf stability.

Example 12

Prepolymer Resins Shelf Stability

The purpose of this example was to evaluate the shelf stability of liquid isocyanate-terminated polyurethane prepolymer resins containing a variety of added tertiary amine activators.

Fifty-gram samples of the prepolymer resins were purged with nitrogen and stored in tightly capped glass jars at 68° C. (150° F.). At time intervals of 3, 7, 10, 14, and 21 days, the jars were removed from the oven, allowed to cool, and inspected for flowability; and, in the case of non-flow, were opened to assess the degree of set (standard viscosity, high viscosity, or solid). This procedure has been described in EP 0086, 621 A1. Non-set or standard viscosity has been claimed to respond to greater than one year of shelf stability. The prepolymer resins used in this example were prepared by combining the ingredients listed in Table 12a. These resins were identical to "Resin-1A", except that DMDEE at 1.0% was replaced by various tertiary amines at 1.0% concentration. The shelf stabilities of prepolymer resins containing various tertiary amines are provided in Table 12b.

TABLE 12a

Prepolymer "Resin-12A"

| Ingredient | Parts (by weight) |
|---|---|
| ISONATE 2143L (Dow Chemical) | 20.39 |
| Polyol ARCOL LHT-28 (ARCO) | 29.90 |
| Polyol ARCOL LHT-42 (ARCO) | 44.41 |
| Pluronic F-108 (BASF) | 3.56 |
| Tertiary Amine | 1.00 |
| BHT (Butylated Hydroxytoluene) | 0.49 |
| Antifoam 1400 (Dow Chemical) | 0.18 |
| p-Toluenesulfonyl Chloride | 0.05 |

TABLE 12b

Shelf Stability of Prepolymer "Resin-12A"

| Run # | Tertiary Amine in "Resin-12A" (1.0%) | Days Stable at 68° C. (Standard Viscosity) |
|---|---|---|
| 1 | DMDEE | Equal to/Greater than 21 |
| 2 | MEMPE (3M Company) | Equal to/Greater than 21 |
| 3 | DMT | Equal to/Greater than 21 |
| 4 | TBDMA | Equal to/Greater than 21 |
| 5 | DHEPT | Less than 7 |
| 6 | DMAPE | Less than 3 |

It is concluded from this example that prepolymer resins containing tertiary amines without hydroxyl (—OH) functional groups (DMDEE, MEMPE, DMT, and TBDMA) have shelf stabilities equal to or greater than 21 days. However, shelf stability was less than 7 days when the resin contained a tertiary amine with one or more hydroxyl groups (DHEPT and DMAPE). It is possible that the hydroxyl group may be participating in an unintended reaction with the isocyanate-terminated prepolymer resin.

Example 13

Reinforcement Composition Shelf Stability

The purpose of this experiment was to initially evaluate the shelf stability of various reinforcement compositions.

Samples of the reinforcement compositions "RC-7C" (Example 1, Table 1c), "RC-7A" (Example 7, Table 7a), and "RC-7B" (Example 7, Table 7a) were prepared with and without the addition of 2.0% BHT (Butylated Hydroxy Toluene) as a potential stabilizer, and then stored in tightly capped glass jars at ambient humidity and temperature. After 14 days, no hardening of any sample was observed.

It is concluded from this initial experiment that a stabilizer is not required in the reinforcement compositions of this example in order to achieve shelf stability of short duration.

Example 14

Reinforcement Composition Dispensing Systems

The purpose of this example was to evaluate various reinforcement composition dispersing systems.

Several different reinforcement formulations and corresponding packaging were prepared as listed in Table 14a.

TABLE 14a

Reinforcement Composition Dispensing Systems

| Run # | Reinforcement Composition | RC "Formulation" | RC "Packaging" |
|---|---|---|---|
| 1 | "RC-7A" (Table 7a) | Viscous Liquid | Lotion Squeeze Bottle |
| 2 | "RC-7B" (Table 7a) | Paste | "Toothpaste" Tube |
| 3 | "RC-1C" (Table 1c) | Added Dimethyl Ether Propellant (7.0%) | Pressurized Container (Fairly thin foam; goes to liquid within 10 sec.) |
| 4 | "RC-7A" | Added Dimethyl Ether Propellant (4.5%) | Pressurized Container (Thick, more durable foam; similar to shaving foam) |

It is concluded from this example that a variety of appropriately formulated reinforcement compositions could be easily dispensed out of a variety of dispensing systems, e.g., squeeze bottles, tubes, pressurized containers, etc. It should be possible to produce a preferred aerosol or foam formulation by varying the amount and type of propellant.

Various modifications and alterations of this invention will be apparent to those skilled in the art without departing from the scope and spirit of this invention, and it should be understood that this invention is not limited to the illustrative embodiments set forth herein.

What is claimed is:

1. A reinforceable orthopedic casting article, comprising: a backing; and
a curable resin comprising an activator, wherein the activator comprises an active reducing component of a redox pair and is present in a sufficient amount to assist in the initiation of the cure of an addition polymerizable reinforcement compound, and thereby reinforce the treated area of the casting article.

2. The casting article of claim 1, wherein the curable resin is selected from the group consisting of water-curable isocyanate-functional prepolymers, polyurethanes, cyanoacrylate esters, epoxy resins, prepolymers terminated at their ends with trialkoxy- or trihalo-silane groups, water-curable alkoxy silane terminated oligomers, and water-reactive liquid organometallic compounds.

3. The casting article of claim 1, wherein the activator is selected from the group consisting of ferrous sulphate, sodium sulphite, sodium dithionite, sodium thiosulphate, ferrous chloride, sodium metabisulphite, organic salts and amines.

4. The casting article of claim 1, wherein the activator comprises a tertiary amine.

5. The casting article of claim 1, wherein the article is in the form of an orthopedic casting tape.

6. The casting article of claim 1, wherein the article is in the form of a soft orthopedic casting tape.

7. A method of making an orthopedic cast, comprising the steps of:
providing a curable casting tape comprising a backing and a curable resin comprising an activator capable of assisting in the initiation of the cure of an addition polymerizable reinforcement compound, wherein the activator comprises an active reducing component of a redox pair, and the reinforcement compound comprises an oxidizing component of the redox pair;

initiating the cure of the casting tape;

wrapping the casting tape into the form of a cast;

applying the reinforcement compound to at least a portion of the casting tape; and allowing the casting tape to cure and the reinforcement compound to harden to form a reinforced orthopedic cast.

8. The method of claim 7, wherein the reinforcement compound is applied to at least a portion of the casting tape between adjacent layers of the wrapped cast.

9. The method of claim 7, wherein the portion of the casting tape that comprises the reinforcement compound comprises a longitudinal strip of the cast.

10. The method of claim 7, wherein the curable resin is selected from the group consisting of water-curable isocyanate-functional prepolymers, polyurethanes, cyanoacrylate esters, epoxy resins, prepolymers terminated at their ends with trialkoxy- or trihalo-silane groups, water-curable alkoxy silane terminated oligomers, and water-reactive liquid organometallic compounds.

11. The method of claim 7, wherein the oxidizing component is selected from the group consisting of dialkyl peroxides and diacyl peroxides.

12. The method of claim 7, wherein the activator comprises a tertiary amine.

13. The method of claim 7, wherein the cast is a soft cast.

14. A method of making an orthopedic cast, comprising the steps of:

wrapping a soft casting tape into the form of a cast, wherein the casting tape comprises a backing and a curable resin;

initiating the cure of the casting tape;

applying an activated addition polymerizable reinforcement compound to at least a portion of the casting tape, wherein the reinforcement compound is selected from the group consisting of multi-part compositions comprising a redox pair that are mixed together prior to being applied to the cast and compositions comprising visible light cure catalyst; and allowing the casting tape to cure and the reinforcement compound to harden to form a reinforced orthopedic cast.

15. The method of claim 14, wherein the curable resin comprises a water-curable resin.

16. The method of claim 14, wherein the mixing is done using a static mixer.

17. The method of claim 14, wherein the reinforcement compound comprises a methacrylate.

18. The method of claim 14, wherein the catalyst is camphorquinone.

19. A kit for making an orthopedic cast, comprising:

a casting tape comprising an activator; and an addition polymerizable reinforcement compound, wherein the activator provided with the casting tape comprises an active reducing component of a redox pair and is present in a sufficient quantity to cause hardening of the reinforcement compound when the reinforcement compound is applied to the casting tape.

* * * * *